US009364651B2

(12) United States Patent
Clark

(10) Patent No.: US 9,364,651 B2
(45) Date of Patent: *Jun. 14, 2016

(54) ADAPTER WITH SPECIAL FITTING

(71) Applicant: SMITHS MEDICAL ASD, INC., Rockland, MA (US)

(72) Inventor: Geoff Clark, Lempster, NH (US)

(73) Assignee: SMITHS MEDICAL ASD, INC., Plymouth, MN (US)

( * ) Notice: Subject to any disclaimer, the term of this patent is extended or adjusted under 35 U.S.C. 154(b) by 547 days.

This patent is subject to a terminal disclaimer.

(21) Appl. No.: 13/785,016

(22) Filed: Mar. 5, 2013

(65) Prior Publication Data
US 2013/0184687 A1 Jul. 18, 2013

Related U.S. Application Data

(63) Continuation-in-part of application No. 12/659,020, filed on Feb. 23, 2010, now Pat. No. 8,876,798.

(51) Int. Cl.
A61M 39/10 (2006.01)
A61M 25/00 (2006.01)
A61M 39/12 (2006.01)

(52) U.S. Cl.
CPC ............ A61M 39/10 (2013.01); A61M 39/1011 (2013.01); A61M 25/0097 (2013.01); A61M 39/12 (2013.01); A61M 2039/1027 (2013.01);
(Continued)

(58) Field of Classification Search
CPC ............ A61M 2039/1077; A61M 2039/1094; A61M 39/10; A61M 39/1011
See application file for complete search history.

(56) References Cited

U.S. PATENT DOCUMENTS 1,871,370 A 8/1932 Jacques
3,170,667 A 2/1965 Szohatzky
(Continued)

FOREIGN PATENT DOCUMENTS

EP 217055 4/1987
EP 774270 5/1997
(Continued)

OTHER PUBLICATIONS

Chinese Office Action issued Apr. 6, 2012 re: CN Appln No. 2011101192607.
(Continued)

Primary Examiner — Imani Hayman
Assistant Examiner — Shefali Patel
(74) Attorney, Agent, or Firm — Louis Woo

(57) ABSTRACT

A clam shell shaped adapter for connecting a fluid output device and a fluid input device to establish a fluid path between the fluid output and input devices has first and second shells integrally connected by a living hinge. The first shell has a connector fitting end and a catheter end connected by a tubing. The fluid output device may be a catheter that is matable to the catheter end. A retainer structure in the adapter fixedly retains the catheter when the first and second shells close upon each other. Respective latch mechanisms provided at the first and second shells lockingly couple the first and second shells to each other. The fitting end has a given configuration that prevents the fitting end from mating with a counterpart conventional luer fitting but enables the fitting end to mate with a counterpart connector fitting that has a special configuration that mirrors the given configuration.

20 Claims, 10 Drawing Sheets

(52) U.S. Cl.
CPC .................. *A61M 2039/1077* (2013.01); *A61M 2039/1094* (2013.01)

(56) References Cited

U.S. PATENT DOCUMENTS

| | | | |
|---|---|---|---|
| 3,287,031 A | 11/1966 | Simmons et al. | |
| 4,006,744 A | 2/1977 | Steer | |
| 4,076,285 A | 2/1978 | Martinez | |
| 4,080,737 A | 3/1978 | Fleer | |
| 4,116,476 A | 9/1978 | Porter et al. | |
| 4,137,917 A | 2/1979 | Cohen | |
| 4,150,673 A | 4/1979 | Watt | |
| 4,211,439 A | 7/1980 | Moldestad | |
| 4,452,473 A | 6/1984 | Ruschke | |
| 4,453,927 A | 6/1984 | Sinko | |
| 4,619,640 A | 10/1986 | Potoisky | |
| 4,682,981 A | 7/1987 | Suzuki et al. | |
| 4,723,948 A | 2/1988 | Clark et al. | |
| 4,758,225 A | 7/1988 | Cox et al. | |
| 4,790,567 A | 12/1988 | Kawano et al. | |
| 4,940,458 A | 7/1990 | Cohn | |
| 4,950,255 A | 8/1990 | Brown et al. | |
| 5,053,015 A | 10/1991 | Gross et al. | |
| 5,069,225 A | 12/1991 | Okamura | |
| 5,078,703 A * | 1/1992 | Bryant | A61M 25/0014 604/243 |
| 5,127,626 A | 7/1992 | Hilal et al. | |
| 5,211,637 A | 5/1993 | Goto et al. | |
| 5,312,337 A | 5/1994 | Flaherty et al. | |
| 5,393,101 A | 2/1995 | Matkovich | |
| 5,405,339 A | 4/1995 | Kohnen et al. | |
| 5,405,340 A | 4/1995 | Fageol et al. | |
| 5,538,399 A | 7/1996 | Johnson | |
| 5,545,152 A | 8/1996 | Funderburk et al. | |
| 5,562,121 A | 10/1996 | Hodges et al. | |
| 5,591,143 A | 1/1997 | Trombley, III et al. | |
| D378,130 S | 2/1997 | Schmidt | |
| 5,605,359 A | 2/1997 | Hoff | |
| D378,405 S | 3/1997 | Musgrave et al. | |
| 5,616,133 A | 4/1997 | Cardenas | |
| 5,620,427 A | 4/1997 | Werschmidt et al. | |
| 5,632,735 A | 5/1997 | Wyatt et al. | |
| 5,651,776 A | 7/1997 | Appling et al. | |
| 5,688,254 A | 11/1997 | Lopez et al. | |
| 5,695,473 A | 12/1997 | Olsen | |
| 5,702,371 A | 12/1997 | Bierman | |
| 5,725,511 A | 3/1998 | Urrutia | |
| 5,741,084 A | 4/1998 | Del Rio et al. | |
| 5,741,269 A | 4/1998 | McCredy | |
| 5,749,861 A | 5/1998 | Guala et al. | |
| 5,810,398 A | 9/1998 | Matkovich | |
| 5,853,391 A | 12/1998 | Bell | |
| 5,855,230 A | 1/1999 | Guala et al. | |
| 5,925,028 A | 7/1999 | Delvigo | |
| 5,947,937 A | 9/1999 | Urrutia et al. | |
| D417,733 S | 12/1999 | Howell et al. | |
| D421,119 S | 2/2000 | Musgrave et al. | |
| 6,027,480 A | 2/2000 | Davis et al. | |
| 6,099,519 A | 8/2000 | Olsen et al. | |
| 6,156,025 A | 12/2000 | Niedospial et al. | |
| 6,171,281 B1 | 1/2001 | Zhang | |
| 6,197,007 B1 | 3/2001 | Thorne et al. | |
| 6,217,564 B1 | 4/2001 | Peters et al. | |
| 6,244,632 B1 | 6/2001 | Gasparini | |
| 6,309,543 B1 | 10/2001 | Fenton et al. | |
| D452,003 S | 12/2001 | Niermann | |
| D452,314 S | 12/2001 | Niermann | |
| 6,350,260 B1 | 2/2002 | Goebel et al. | |
| 6,402,207 B1 | 6/2002 | Segal et al. | |
| 6,422,607 B1 | 7/2002 | Kirby | |
| 6,428,514 B1 | 8/2002 | Goebel et al. | |
| 6,475,190 B2 | 11/2002 | Young | |
| 6,500,153 B1 | 12/2002 | Sheppard et al. | |
| 6,506,181 B2 | 1/2003 | Meng et al. | |
| 6,511,472 B1 | 1/2003 | Hayman et al. | |
| 6,524,304 B1 | 2/2003 | Picou et al. | |
| 6,536,805 B2 | 3/2003 | Matkovich | |
| 6,558,353 B2 | 5/2003 | Zohmann | |
| 6,612,624 B1 | 9/2003 | Segal et al. | |
| 6,656,161 B2 | 12/2003 | Young et al. | |
| 6,676,652 B2 | 1/2004 | Mogg | |
| 6,688,651 B2 | 2/2004 | Min-cheol | |
| 6,722,705 B2 | 4/2004 | Korkor | |
| 6,786,131 B2 | 9/2004 | Tsai | |
| 6,802,836 B2 | 10/2004 | Bouphavichith et al. | |
| 6,843,513 B2 | 1/2005 | Guala | |
| 6,893,056 B2 | 5/2005 | Guala | |
| 6,953,448 B2 | 10/2005 | Moulton et al. | |
| 6,988,423 B2 | 1/2006 | Bolam et al. | |
| 7,044,936 B2 | 5/2006 | Harding et al. | |
| 7,115,228 B2 | 10/2006 | Lundtveit et al. | |
| 7,240,927 B2 | 7/2007 | Chang | |
| 7,270,349 B2 | 9/2007 | Bamberger et al. | |
| 7,344,527 B2 | 3/2008 | Schweikert et al. | |
| 7,481,796 B2 | 1/2009 | Nishtala et al. | |
| 7,571,889 B2 | 8/2009 | Miyahara | |
| 7,635,354 B2 | 12/2009 | Navarro | |
| 7,641,648 B2 | 1/2010 | Bouphavichith et al. | |
| 7,857,805 B2 | 12/2010 | Raines | |
| 7,955,315 B2 | 6/2011 | Feinberg et al. | |
| 2001/0049490 A1 | 12/2001 | Slanda et al. | |
| 2002/0079258 A1 | 6/2002 | Sawa | |
| 2002/0151838 A1 | 10/2002 | Beck et al. | |
| 2003/0105428 A1 | 6/2003 | Hogan et al. | |
| 2004/0162544 A1 | 8/2004 | Raulerson et al. | |
| 2004/0167474 A1 | 8/2004 | Meng et al. | |
| 2004/0201216 A1 | 10/2004 | Segal et al. | |
| 2005/0090801 A1 | 4/2005 | Racz et al. | |
| 2005/0209581 A1 | 9/2005 | Butts et al. | |
| 2005/0225082 A1 | 10/2005 | Dalle et al. | |
| 2006/0015086 A1 | 1/2006 | Rasmussen et al. | |
| 2007/0076401 A1 * | 4/2007 | Carrez et al. | 361/816 |
| 2007/0088329 A1 | 4/2007 | Bierman | |
| 2007/0225683 A1 | 9/2007 | Raulerson et al. | |
| 2007/0270758 A1 | 11/2007 | Hanner et al. | |
| 2008/0177250 A1 | 7/2008 | Howlett et al. | |
| 2008/0183154 A1 | 7/2008 | Racz et al. | |
| 2008/0287919 A1 | 11/2008 | Kimball | |
| 2008/0294146 A1 | 11/2008 | Charlez | |
| 2008/0312640 A1 | 12/2008 | Grant | |
| 2009/0187165 A1 | 7/2009 | Kaern | |
| 2009/0187166 A1 | 7/2009 | Young | |
| 2009/0204105 A1 | 8/2009 | Johansson et al. | |
| 2009/0243281 A1 | 10/2009 | Seifert et al. | |
| 2009/0270842 A1 | 10/2009 | Blocher et al. | |
| 2009/0292273 A1 | 11/2009 | Racz et al. | |
| 2009/0299339 A1 | 12/2009 | Young | |
| 2010/0022951 A1 | 1/2010 | Ferrera et al. | |
| 2010/0094260 A1 | 4/2010 | Cude et al. | |

FOREIGN PATENT DOCUMENTS

| | | |
|---|---|---|
| EP | 1010439 | 6/2000 |
| FR | 2642139 | 7/1990 |
| GB | 771967 | 4/1957 |
| JP | H11-319114 | 11/1999 |
| JP | 2001-187990 | 7/2001 |
| WO | 97-32618 | 9/1997 |
| WO | 2005/044335 | 10/2004 |
| WO | 2006-125789 | 11/2006 |

OTHER PUBLICATIONS

Canadian Office Action issued Apr. 13, 2012 re: CA Appln No. 2575136.

Sheppard et al., "Improving patient safety by design—a new spinal/intrathecal injection safety system", Can J Anesth 2006; 0108-9.

* cited by examiner

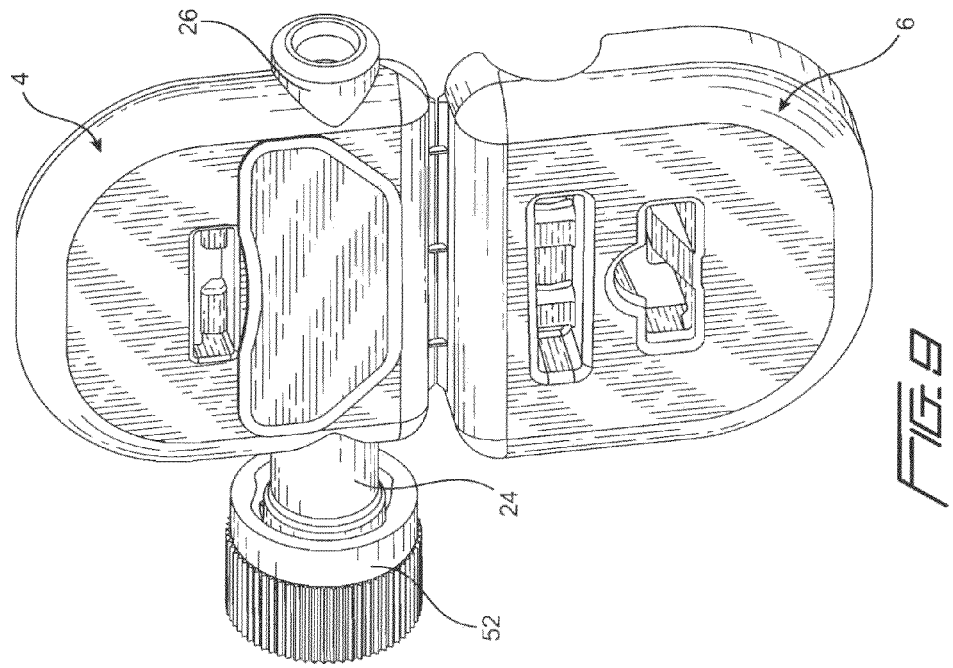
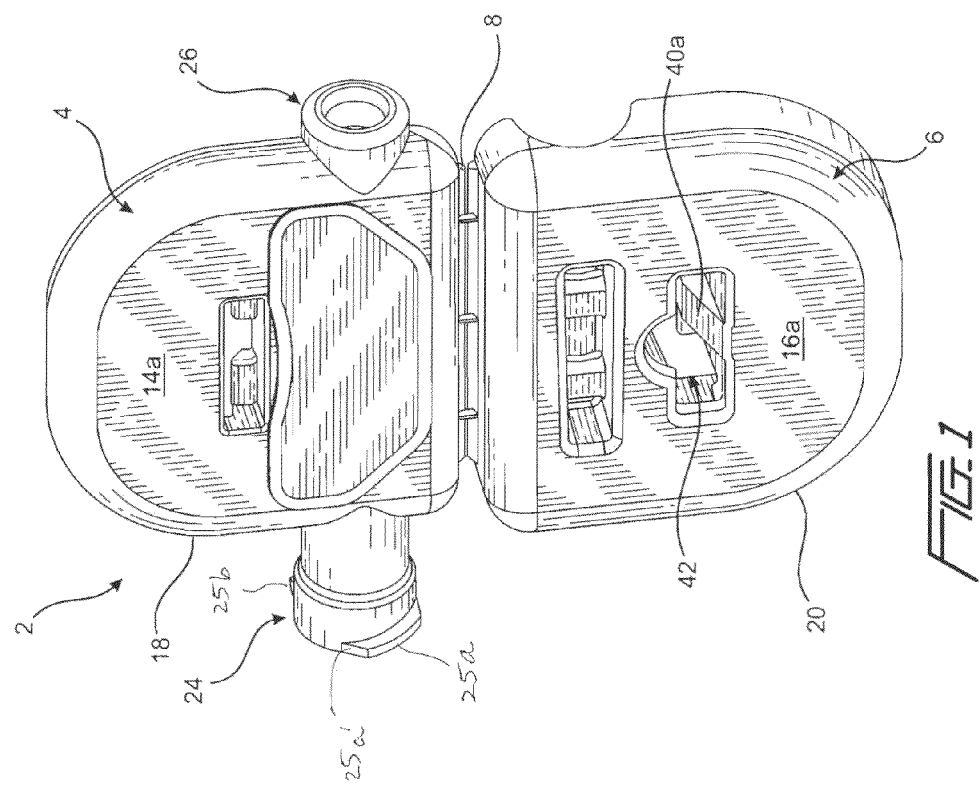

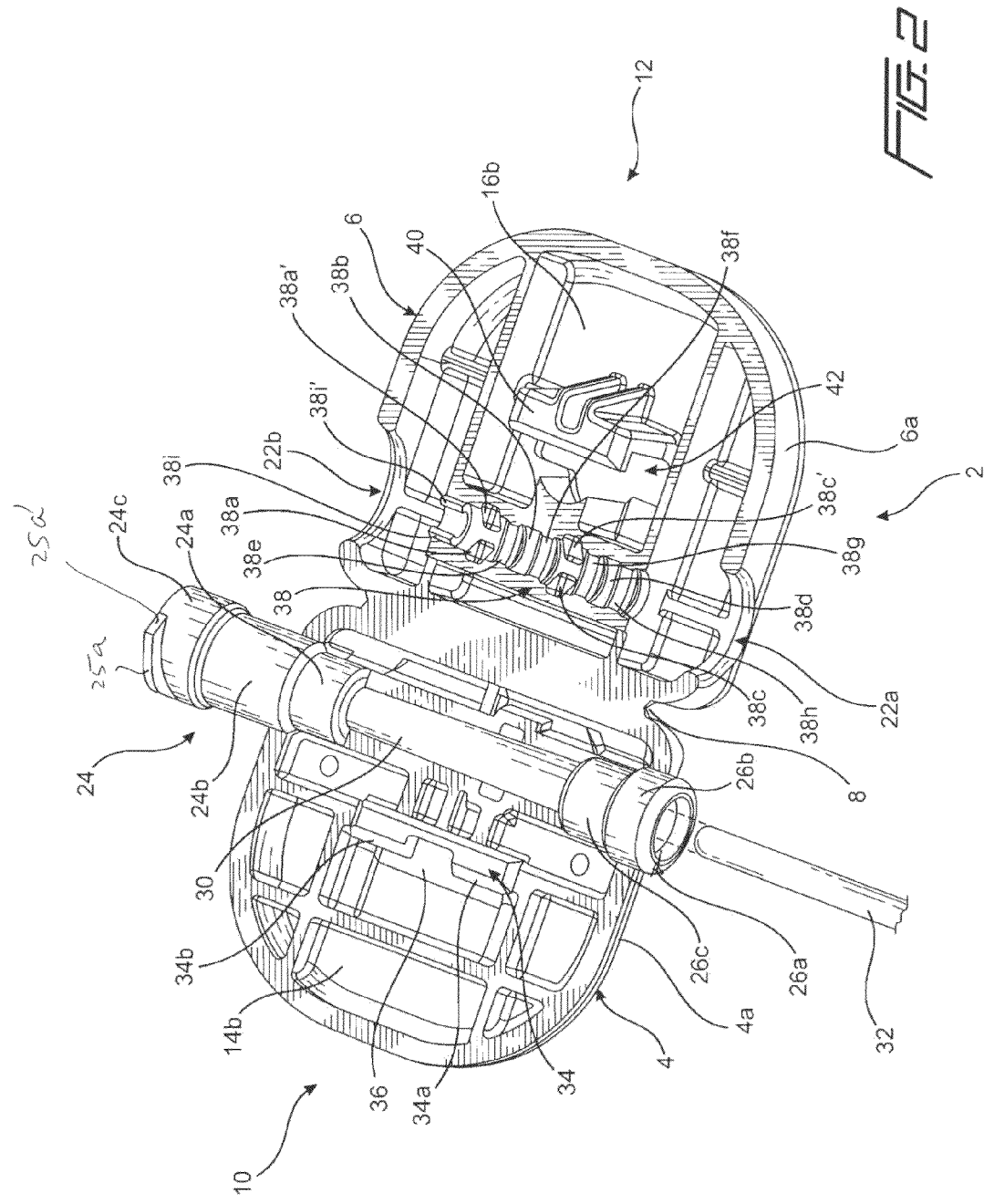

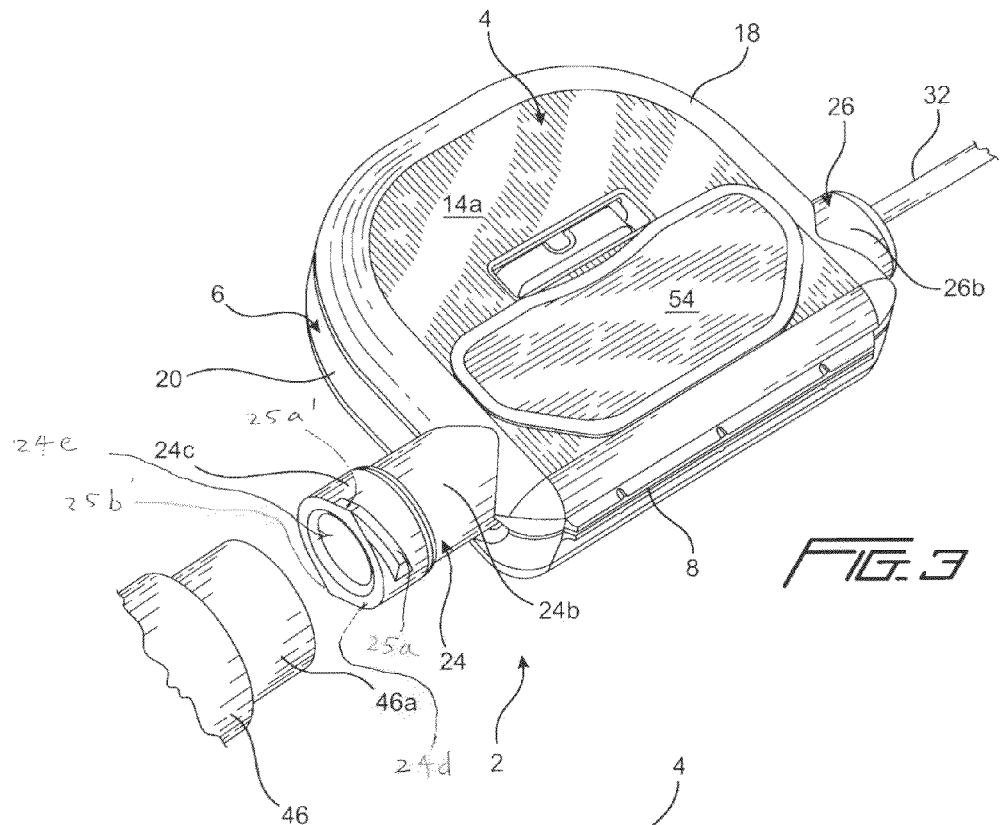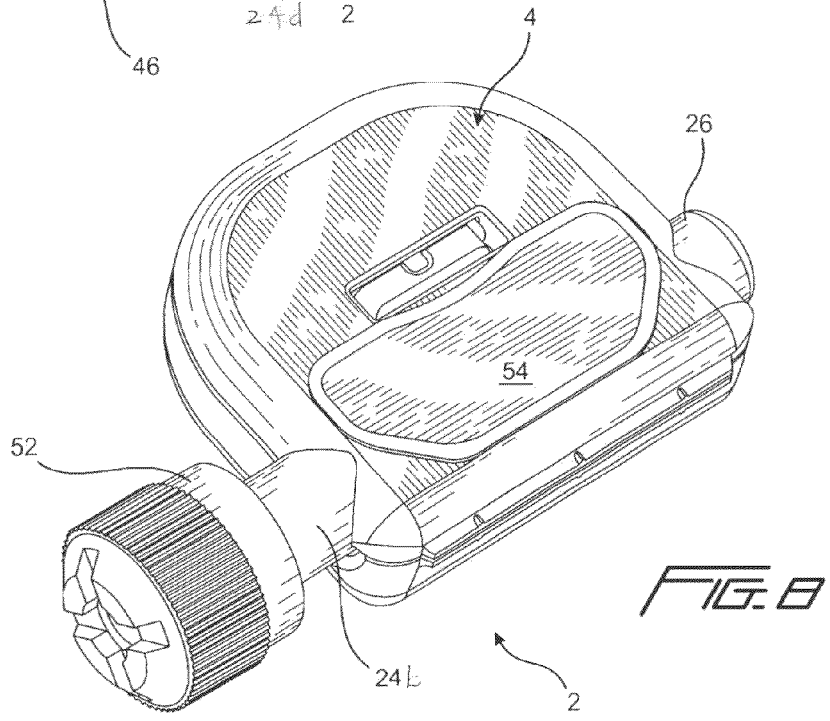

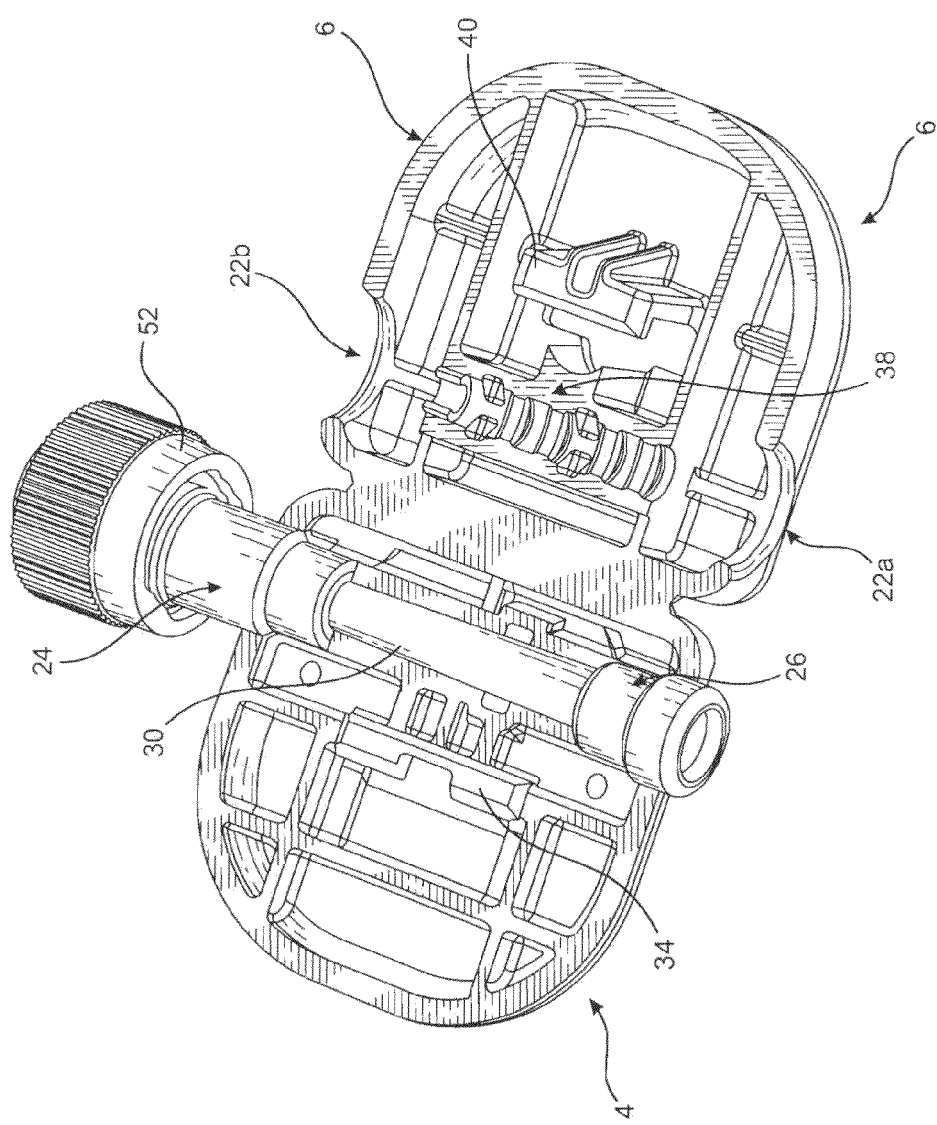

ADAPTER WITH SPECIAL FITTING

CROSS REFERENCES TO RELATED APPLICATIONS

This application is a continuation-in-part application of application Ser. No. 12/659,020 filed on Feb. 23, 2010.

FIELD OF THE INVENTION

The present invention relates to a medical device for coupling a catheter to a fluid delivery or storage device, and more particularly to an adapter for connecting a catheter to a fluid delivery or storage device that has its latching mechanisms remotely located from the exterior surfaces of the adapter to prevent accidental uncoupling of the catheter. The invention further is directed to a special receptacle fitting for the medical device that enables it to be connected only to a fluid transfer device with a counterpart of the special fitting.

BACKGROUND OF THE INVENTION

Catheter connector devices for coupling a catheter to a fluid delivery or storage device such as a syringe or a medicament fluid line is known. Such devices may be used for medical procedures including an epidural injection procedure whereby a catheter is inserted into a patient's epidural space so that medicament may be injected to the patient to locally anesthesize the patient for example during child birth. Before an epidural catheter can be inserted into the epidural space of the patient, an epidural needle is first inserted into the epidural space. Thereafter an epidural catheter is guided by the needle into the epidural space of the patient and the epidural needle is removed. A catheter connector device then connects the free end of the catheter to a syringe, a fluid line or other fluid store means that has the medicament. The prior art medical catheter connector devices would clamp the catheter and provide an end whereby the luer of the syringe, fluid line or other fluid store means may be connected so that a fluid path is established between the catheter and the syringe, fluid line or other fluid store means. Some prior art catheter connectors are disclosed in U.S. Pat. Nos. 5,078,703, 4,006,744, 6,350,260, 7,635,355, and U.S. publication Nos. 2006/0271000, 2008/0183154.

Most, if not all of the noted patents and publications disclose devices having locking mechanisms that are exposed, so that there may be accidental uncoupling of the catheter. The others of those disclosed devices require the relative twisting and turning of portions of the devices to align the catheter with the fluid store means, if the fluid store means happens to be a fluid line.

The instant invention catheter adapter overcomes the disadvantages of the prior art catheter connectors.

SUMMARY OF THE PRESENT INVENTION

The medical adapter of the instant invention is a one piece clam shell shaped device made of medical plastics such as polypropylene that includes two shells that are integrally connected by a common living hinge. The shells have counter matching peripheries so that when folded along the living hinge with their respective inner surfaces facing each other or in opposed relationship to each other, the peripheries of the shells matchingly abut. The shells are formed such that one of the shells is thinner than the other. The thinner shell has molded thereat a luer end at one end and an aperture end for accepting a catheter at its other end along a longitudinal axis that runs parallel and adjacent to the living hinge. An elastomeric flexible tubing or tube connects the luer end to the aperture end at the inner surface of the thinner shell so that a through path is established between the luer end and the aperture end. As the flexible tube connected luer and aperture ends are aligned adjacent to the living hinge, they are positioned offset from the center of the shell.

At the approximate center of the thinner shell that has the luer and aperture ends, there is formed at the inner surface a latch mechanism that comprises a catch.

At the other shell, which is the thicker of the two shells, of the medical device of the instant invention there is formed at approximately the center thereof at its inner surface another latch mechanism in the form of a finger that would snappingly grasp the catch at the other shell, when the two shells are movingly folded along the living hinge towards each other. When the shells are closed onto each other with their respective peripheries matchingly abut, the two shells are firmly engaged to each other due to the finger at the thicker shell lockingly coupled to the catch at the thinner shell. When thus coupled, a retainer surface structure at the inner surface of the thicker shell presses against the flexible tubing at the inner surface of the thinner shell to fixedly hold or retain the catheter that has been inserted through the aperture end into the flexible tubing.

A notch or cavity to enable the decoupling of the shells is provided from the outer surface to the interior of the shell that has the latch finger. A pointed object such as a conventional male luer slip end of a syringe can be inserted into the notch to push against a boss at the back of the finger to disengage the finger from the catch, to thereby decouple the two shells and remove the pressure applied to the flexible tubing by the retainer structure. The catheter inserted to and extending along the flexible tubing could then be withdrawn from the device.

Another feature of the instant invention device is that the formation of the flexible tubing is by injection molding an elastomeric material through a bore at the outer surface of the thinner shell so that the injected elastomeric material would congeal to form the flexible tubing that connects the luer fitting end to the aperture end. During the injection molding process, a soft elastomeric pad that enhances the ease with which a user can grasp the adapter is formed at the outer surface of the shell.

The present invention therefore relates to a one piece catheter connector device that comprises a first member or one shell and a second member or an other shell each having an inner surface and an outer surface. The one and other shells are integrally connected at a common living hinge and have respective matching peripheries to form a clam shell shaped member. The one shell has formed thereat a luer end and an aperture end connected by a flexible tubing at its inner surface so that a through passage is established between the luer end and the aperture end. The aperture end is adapted to accept a catheter input to said flexible tubing. The one shell has a first latch mechanism at its approximate center and the other shell has a second latch mechanism at its approximate center that lockingly engage to couple the one and other shells to each other when the one and other shells are folded along the common living hinge to move the respective inner surfaces of the one and other shells to face each other. The other shell includes a retainer structure at its inner surface that presses against the flexible tubing to fixedly hold or retain the catheter in the flexible tubing when the one and other shells are coupled to each other.

The instant invention also relates to an adapter for coupling a catheter to a fluid store or a fluid line that comprises a one piece clam shell shaped member having one shell and other shell integrally attached to and foldable toward each other by a living hinge. The one shell and other shell each have an inner surface and an outer surface. The one shell has formed thereat a luer end and an aperture end connected by a flexible tubing at its inner surface so that a through passage is established between the luer end and the aperture end. The aperture end is adapted to accept a catheter input to said flexible tubing. A first latch mechanism at approximately the center of the one shell lockingly engages a second latch mechanism at approximately the center of the other shell when the one and other shells are folded along the living hinge to close upon each other. A retainer structure at the inner surface of the other shell presses against the flexible tubing to fixedly hold or retain the catheter in the flexible tubing when the first and second latch mechanisms are engaged to each other.

The instant invention is further related to an apparatus that comprises a catheter, a fluid store means; and an adapter that includes a one piece clam shell shaped member having one shell and other shell integrally attached to and foldable toward each other by a living hinge. The one shell and the other shell each have an inner surface and an outer surface. The one shell has formed thereat a luer end and an aperture end connected by a flexible tubing at its inner surface so that a through passage is established between the luer end and the aperture end. The aperture end is adapted to accept the catheter into the flexible tubing and the luer end is adapted to mate with a counterpart luer at the fluid store means. A first latch mechanism at the one shell lockingly engages a second latch mechanism at the other shell when the one and other shells are folded along the living hinge to close upon each other. A retainer structure at the inner surface of the other shell presses against the flexible tubing to fixedly hold or retain the catheter when the first and second latch mechanisms are engaged to each other, whereby a fluid path between the catheter and the fluid store means is established by the adapter.

BRIEF DESCRIPTION OF THE FIGURES

The present invention will become apparent and the invention itself will be best understood by reference to the following description of the present invention taken injunction with the accompanying drawings, wherein:

FIG. 1 is a perspective view of the catheter adapter coupling device of the instant invention showing both shells of the device along the same plane;

FIG. 2 shows the device of FIG. 1 with the inner surfaces of both shells of the device exposed along the same plane;

FIG. 3 shows the device of the instant invention with both shells of the device closed upon each other to form a closed and/or coupled device;

FIG. 8 shows in perspective a locked device of the instant invention with its luer end protected by a protective cover cap;

FIG. 9 is a perspective view of the outer surfaces of both shells of the device lying a coplanar relationship, with the luer end threadedly mated to a protective cover cap;

FIG. 10 corresponds to FIG. 2 but with the luer end threadedly mated to a protective cover cap;

DETAILED DESCRIPTION OF THE INVENTION

Figure 5:
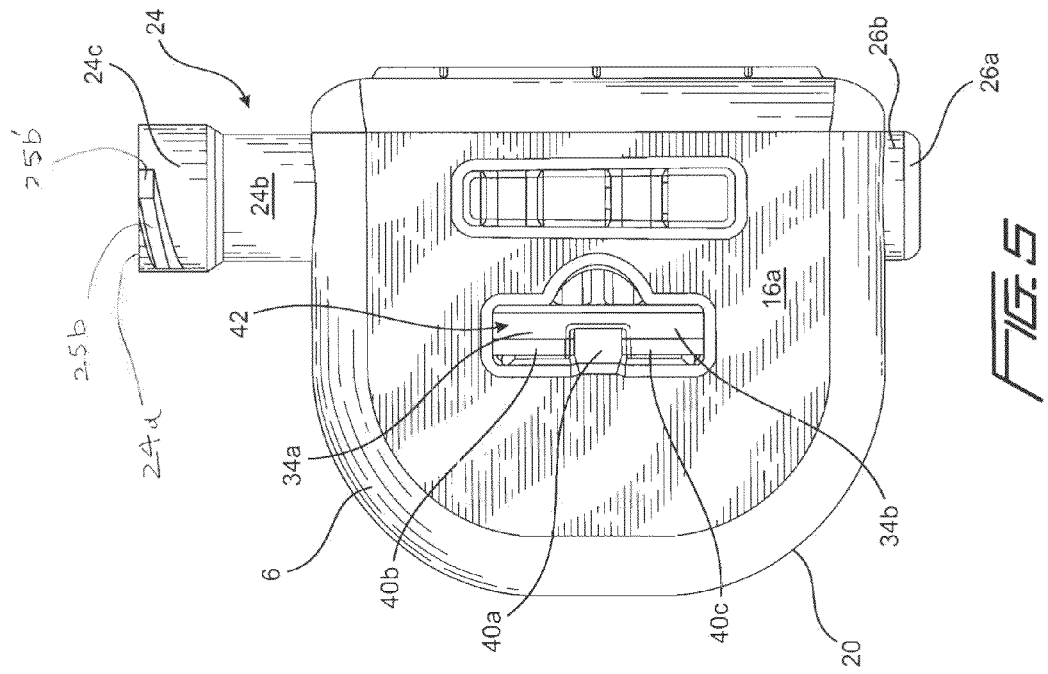
FIG. 5 is a plan view of the outer surface of the other shell of the device of the instant invention showing a notch or cavity that exposes the boss of the finger latch mechanism located at the interior of the device.

With reference to FIGS. 1-5, the medical catheter adapter 2 of the instant invention is a combination coupler and retainer device for connecting a catheter, for example an epidural catheter, to a fluid storage or fluid delivery device such as a syringe and a fluid line. In particular, device 2 is shown to be a single unitary device in the shape of a clam shell that has a first member or one shell 4 and a second member or other shell 6 integrally connected by a common living hinge 8 so that the shells are movable relative towards each other per the directions designated by directional arrows 10 and 12 to close upon each other in the closed position per shown in FIG. 3.

As shown in FIGS. 1 and 2, shell 4 has an outer surface 14a and an inner surface 14b, while shell 6 has an outer surface 16a and an inner surface 16b. For the most part, the peripheries 18 and 20 of shells 4 and 6, respectively, have counterpart matching configurations, so that when device 2 is in the closed position as shown in FIG. 3, peripheries 18 and 20 matchingly abut to form a closed container with no external edges from either of the shells showing beyond the common peripheries 18 and 20. Accordingly, the catheter adapter 2 of the instant invention, when in its closed and/or coupled position, is a compact device with a smooth boundary except for two connection ports as will be described, infra.

As shown in FIG. 2, the thickness of shell 4, designated 4a, is less than the thickness 6a of shell 6. In other words, shell 4 is a thinner shell than shell 6, which periphery 20 includes semi-circumferential openings 22a and 22b having respective curvatures that allow shells 4 and 6 to close in light of the connection ports formed at shell 4.

In particular, shell 4 has formed as a part thereof and extending mostly from its inner surface 14b two connection ports that may be referred to as a luer fitting end (or luer end) 24 and a catheter fitting aperture end (or an aperture end) 26. As device 2 comprises a one piece body that is molded of medical plastics material such as polypropylene, luer end 24 and aperture end 26 are formed at the same time that device 2 is molded so that device 2, before the injection molding of an elastomeric material thereto, is per shown in FIGS. 6 and 7.

Luer end 24 comprises a base 24a, a mid-section 24b and a fitting end 24c. The outside diameter of mid-section 24b is configured to be slightly less than the semi-circumferential opening 22b at shell 6 so that opening 22b would form fit over mid-section 24b when shells 4 and 6 are moved relative to each other per the direction shown by directional arrows 10 and 12 for closing and coupling the shells.

Aperture end 26, which may also be referred to as a catheter end, has an aperture opening 26a, a front end 26b and a base 26c. The outside diameter of front end 26b is configured to be slightly less than the semi-circumferential opening 22a of shell 6 so that opening 22a would form fit over front end 26b when shells 4 and 6 are closed per shown in FIG. 3.

To establish a through path between luer end 24 and aperture end 26, an elastomer is injection molded though a bore 28 (FIGS. 6 and 7) from the outer surface 14a of shell 4 so that an elastomeric flexible tube or tubing 30 is formed at the inner surface 14b of shell 4 for establishing a through passageway between luer end 24 and aperture end 26. Although not clearly shown, the elastomeric material extends partially into base portion 24a of luer end 24 at one end and is flush with aperture opening 26a of aperture end 26. Catheter 32, for example an epidural catheter, is insertable through aperture opening 26a into aperture end 26, and from there extends through flexible tubing 30 into base 24a of luer end 24. The insertion movement of the catheter is stopped by an internal shoulder (not shown) at the junction of base 24a and mid-section 24b of luer end 24.

Figure 7:
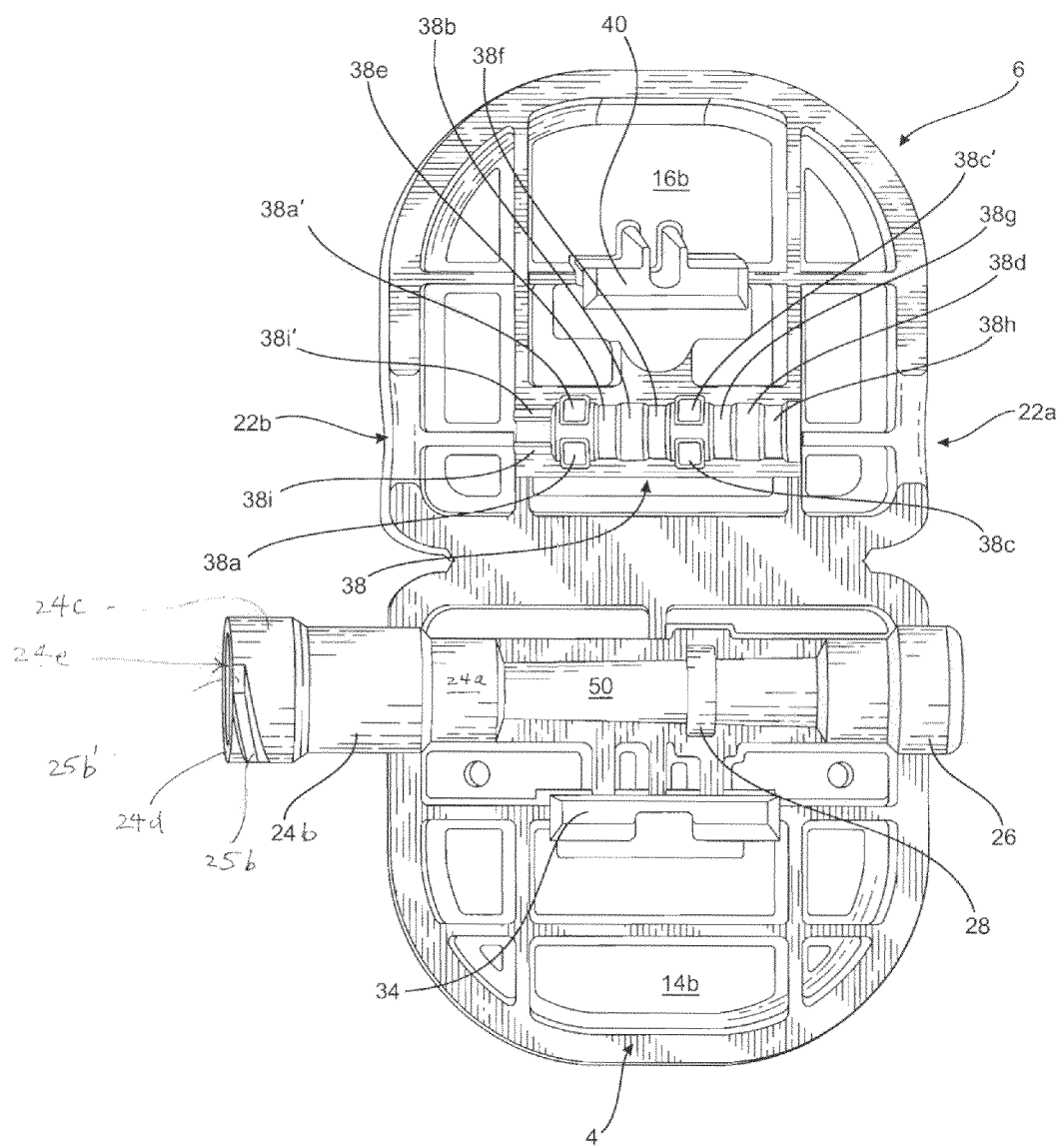
FIG. 7 is a perspective view of the inner surfaces of the two shells of the instant invention medical device before the injection molding process of forming the flexible tubing in the device
Figure 11:
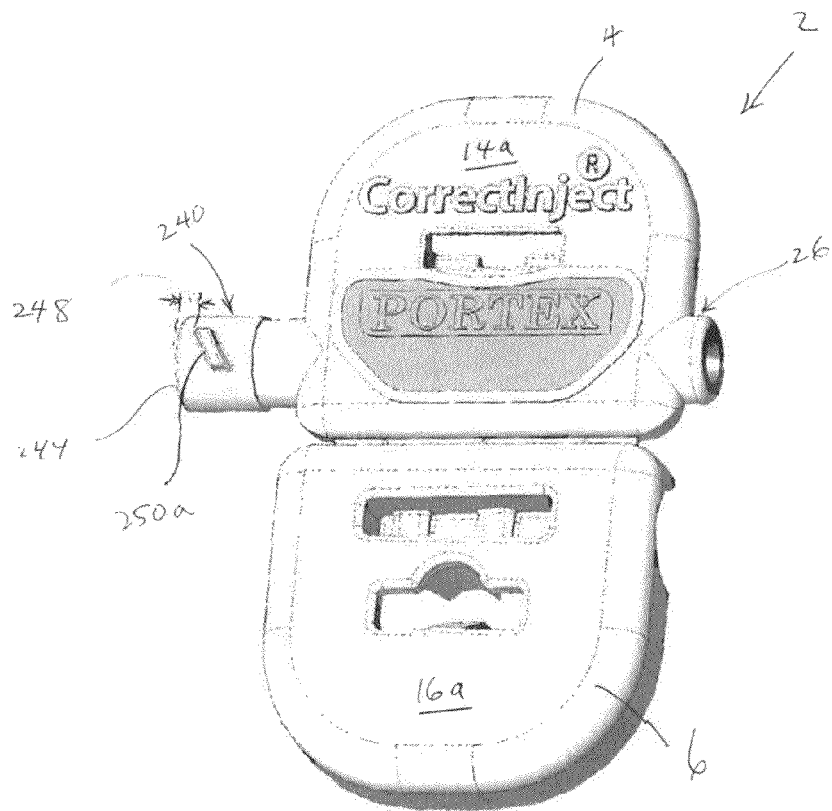
FIG. 11 is an alternative embodiment of the catheter adapter coupling device of the instant invention.
Figure 12:
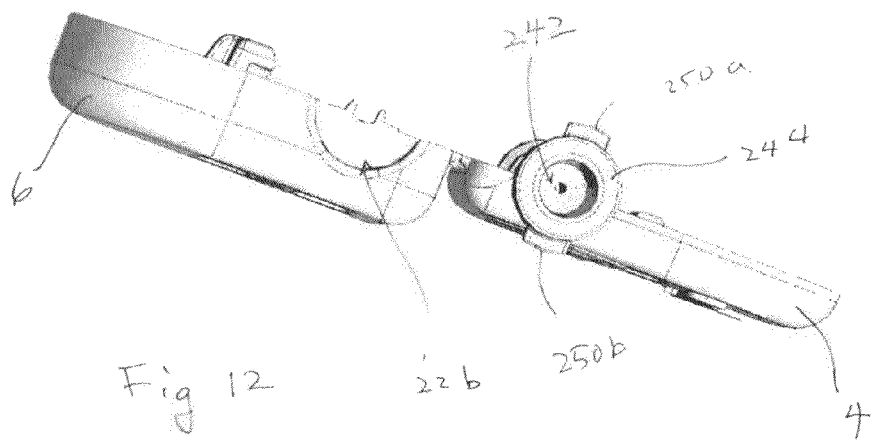
FIG. 12 shows a perspective side view of the FIG. 11 device.

At inner surface 16b of shell 6 there is integrally formed a retainer structure 38 that has a length substantially the same as the length of the flexible tubing between base 26c of aperture end 26 and base 24a of luer fitting end 24. As illustrated in FIGS. 2 and 7, retainer structure 38 may comprises a plurality of recesses 38a and 38a', 38b, 38c and 38c', and 38d, interspaced with a plurality of ribs 38e, 38f, 38g and 38h. The respective plurality of recesses and ribs together form a ribbed surface that slightly curves inwardly towards the inner surface 16b of shell 6 for contacting flexible tubing 30. Also being part of retainer structure 38 are two spatially opposed protrusions 38i and 38i' positioned at the end of the retainer structure that is proximate to semi-circumferential opening 22b.

The ribbed surface of retainer structure 38 is configured to enable it to form fittedly press against flexible tubing 30 so that those portions of the elastomeric material of flexible tubing 30 that come into contact with the ribs are compressed by the ribs while those portions of the elastomeric material that end up being in opposed relationship to the recesses would remain substantially uncompressed so as to extend into the recesses. Thus, when shells 4 and 6 are moved to close upon each other, retainer structure 38—and in particular its ribbed contact surface formed by the protrusions 38i and 38i', the recesses 38a and 38a', 38b, 38c and 38c', and 38d, and the ribs 38e, 38f, 38g and 38h—would press against flexible tubing 30 such that there is a form fitting compressed crimping of the elastomeric material of the flexible tubing 30 by the respective recesses, ribs and protrusions of the retainer structure 38, so that catheter 32 positioned lengthwise inside flexible tubing 30 is held fixedly therein in a fluid sealingly tight relationship. Putting it differently, with the portion of retainer structure 38 that makes contact with flexible tubing 30 configured per shown in FIGS. 2 and 7, once the shells 4 and 6 are lockingly coupled to each other, as will be described infra, retainer structure 38 acts to establish a fluid tight seal between catheter 32 and flexible tubing 30 as well as to fixedly retain catheter 32 and flexible tubing 30 relative to each other. Also, the recesses, ribs and protrusions of retainer structure 38 are configured to have dimensions that ensure that there is no crimping of the catheter when retainer structure 38 compresses flexible tubing 30, so as not to impede the flow of fluid through catheter 32.

Thus, when shells 4 and 6 are moved via living hinge 8 to close upon and securely coupled to each other, per shown in FIG. 3, retainer structure 38 will press against flexible tubing 30 to fixedly hold catheter 32 along flexible tubing 30 without crimpingly distorting the through passage of catheter 32, and at the same time provide a fluid tight seal between catheter 32 and flexible tubing 30 to prevent fluid leakage from flexible tubing 30 and therefore the adapter. Catheter 32 is not removable from device 2 until shells 4 and 6 are uncoupled and disengaged from each other.

Further with respect to shell 4, formed integrally at the inner surface 14b thereof is a latch mechanism in the shape of an interrupted catch 34 that includes catch members 34a and 34b. An opening 36 connects inner surface 14b to outer surface 14a of shell 4.

Figure 6:
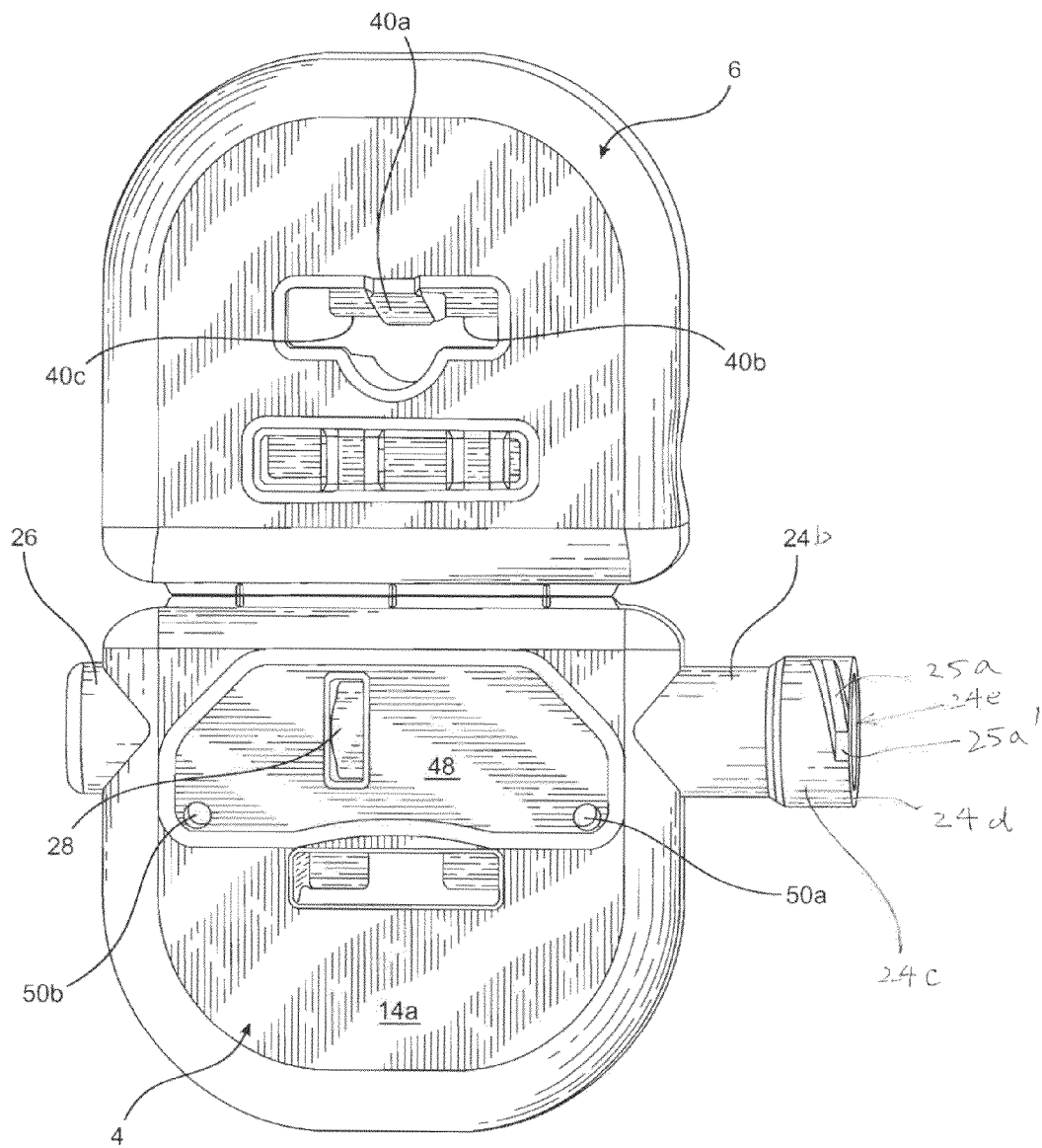
FIG. 6 is a perspective view of the outer surfaces of the two shells of the instant invention medical device before the injection molding process of forming the flexible tubing in the device.

To couple shells 4 and 6 in a locking relationship, integrally extending from inner surface 16b of shell 6 is another latch mechanism in the form of a latch finger 40 interrupted at its middle by a boss 40a (FIGS. 1 and 5) so that finger 40 may be considered to be divided into gripping finger portions 40b and 40c (FIGS. 5 and 6).

With latch mechanisms 34 and 40 in cooperation, when shells 4 and 6 are folded along living hinge 8 so that their respective inner surfaces 14b and 16b face each other, with latch finger 40 snap fitted to catch 34, the adapter device 2 of the instant invention becomes a closed clam shell shaped container, per shown in FIG. 3, with the catheter 32 inserted along flexible tube 30 via aperture end 26 being fixedly held or retained to flexible tubing 30 by retainer structure 38 of shell 6. A fluid through path or passageway is thereby established between luer end 24 and catheter 32.

Figure 4:
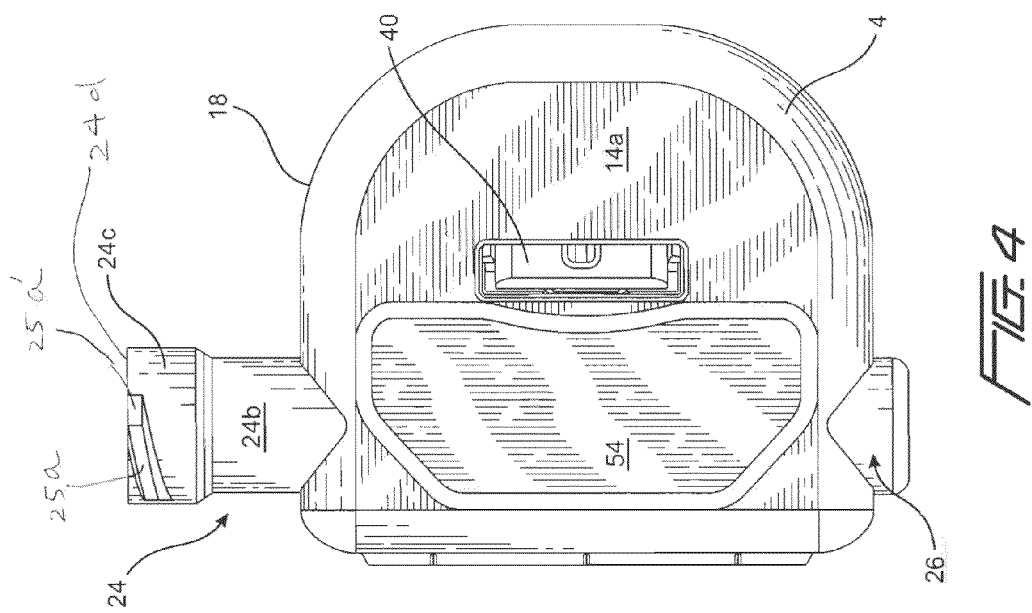
FIG. 4 is a plan view of the outer surface of the one shell of the device of the instant invention having an elastomeric pad and an opening exposing the catch latch mechanism of the device.

As shown in FIGS. 3-5, as the latch mechanisms 34 and 40 are located in the interior of the closed clam shell shaped device, they are therefore remotely located from the respective outer surfaces 14a and 16a of shells 4 and 6 of adapter device 2. Moreover, as each of latch mechanisms 34 and 40 is located at approximately the center of its corresponding shells 4 and 6, latch mechanisms 34 and 40 are also located remotely from the peripheries 4a and 6a of shells 4 and 6. As a result, once engaged in a locking relationship, the latch mechanisms 34 and 40 are not exposed to the environment, and therefore could not easily be tampered with, or be accidentally disengaged and/or uncoupled from each other.

So that shells 4 and 6 could be uncoupled from each other, a disengagement or decouple through hole or notch 42 is provided at outer surface 16a of shell 6 to enable a direct view into exposed latch finger 40, which is in a locking relationship with catch 34. A pointed object such as the male slip end of a syringe may be inserted into notch 42 to press against boss 40a to force latch finger 40 away from catch 34 (specifically catch members 34a and 34b), thereby uncoupling shells 4 and 6 from each other. Once shells 4 and 6 are uncoupled or disengaged from each other, flexible tube 30 is no longer pressedly held by retainer structure 38. Accordingly, catheter 32 can be removed from flexible tubing 30.

To supply medicament to a patient who has a catheter such as catheter 32 inserted in her, assuming that catheter 32 has been inserted into and extends along flexible tubing 30 and shells 4 and 6 of device 2 are lockingly coupled so that catheter 32 is fixedly retained in device 2, a fluid store such as a syringe 46 with a luer end 46a may be threadedly mated to luer 24c of luer end 24 so that the medicament in syringe 46 may be conveyed to catheter 32 and from there delivered to the patient. For the instant invention, luer end 24 may be a conventional luer that is adapted to mate with a conventional counter luer of a conventional syringe, such as 46a shown in FIG. 3. For syringes or fluid lines that are specially designed to have a particular configuration or dimension, luer end 24 could be similarly configured to mate with those specially designed fluid delivery and storage devices. That luer end 24 may be configured to have a given configuration that is a counterpart to the specially designed fitting end of a fluid supply device so that adapter device 2 and the specially designed fluid store device are matable to each other will be discussed in further detail, infra.

As discussed above, flexible tubing 30 is formed by the injection molding of an elastomeric material through bore 28 of shell 4. As best shown in FIG. 6, there is a shallow pond or cavity 48 formed on outer surface 14*a* which, in addition to main bore 28 also has smaller bores 50*a* and 50*b*. During the injection process, the elastomeric material is injected though bore 28 (with the appropriate die in opposed relationship to inner surface 14*b*) to form the flexible tubing 30 between luer fitting end 24 and aperture end 26 in the mold space 50 at the inner surface 14*b* of shell 4, per shown in FIG. 7. An appropriate journal or pin-like rod extending between luer fitting end 24 and aperture end 26 effects the through passageway for flexible tubing 30 during the injection molding process.

In addition to flexible tubing 30, during the injection molding process, the elastomeric material also forms a flexible elastomeric pad 54 at shallow pond 48 flush with the outer surface 14*b* of shell 4. The thus formed elastomeric pad 54, anchored to bores 50*a* and 50*b*, in addition to possibly having some indicia for example the name of the assignee embossed thereon, provides the user with a touch responsive elastomeric pad for better grasping device 2. Thus, the injection molding of an elastomeric material to shell 4 not only forms the flexible tubing 30 at inner surface 14*b* of shell 4, it also forms a soft elastomeric finger pad 54 at outer surface 14*a* of shell 4.

To provide sterility for the luer end 24, a protective cover cap 52 may be threadedly mated to luer end 24 of the device, per shown in FIGS. 8-10.

Although the adapter device of the instant invention is disclosed for use with an epidural catheter, it should be appreciated that the adapter device as disclosed could also be used for other types of catheters or fluid output devices by merely changing the diameter of the aperture end, i.e., the catheter connection port. So, too, although the luer end described is a conventional luer that is adapted to be used with a conventional counterpart luer, the dimensions of the luer end may be varied to mate with fittings of special configurations and dimensions to establish a fluid path between the fluid delivery, transfer or storage device and the catheter FIGS. 11-15A and 15B show an alternative embodiment of the instant invention adapter where its luer fitting end is configured with a predetermined given configuration. For the figures of the alternative embodiment, the components that are the same or function the same as in the earlier embodiment are labeled the same. Most of the components between the alternative embodiment and the earlier described embodiment are the same. The one component in the alternative embodiment that is different from the earlier embodiment is the luer fitting end, or fitting end 240, of the adapter device shown in FIGS. 11-14.

With reference to FIGS. 1-3, for the adapter of the earlier embodiment, the luer fitting end 24 is shown to be a cylindrical extension that has a base 24*a*, a mid-section 24*b* and a fitting end 24*c*. The luer end fitting 24 has a distal end 24*d* where the opening 26*a* forms the mouth of the through bore of cylindrical extension 24. Formed at the fitting end 24*c* are two protrusions 25*a* and 25*b* that integrally extend from fitting end 24*c* with their respective distal ends 25*a*' and 25*b*' starting at the distal end 24*d*. The protrusions 25*a* and 25*b* are elongate ribs that are formed in accordance with well established standard dimensions so that luer fitting end 24 is matable with a conventional counterpart luer fitting, for example luer end 46*a* of syringe 46 per shown in FIG. 3. Also, opening 24*e* of the special configuration fitting end 24 has a conventional cross sectional dimension, so that it can accept a conventional nose extension (not shown) that may be a part of a conventional male luer fitting such as fitting 46*a* of syringe 46. The problem with having a conventional luer connector fitting, such as the exemplar conventional female luer fitting end 24 for adapter 2 shown in FIGS. 1-3, is that adapter 2 may mistakenly be connected to other fluid store or supply devices including for example syringes, fluid bags or fluid input lines with counterpart conventional connector fittings that are not meant to be connected to the adapter 2. As a result, the wrong medicament stored in a mistakenly connected fluid supply device may be input to the patient, thereby leading to potential disastrous consequences for the patient.

The adapter embodiment of FIGS. 11-14 eliminates the possibility that the adapter of the device of the instant invention may be mistakenly connected to a wrong fluid input device or fluid line. To achieve this, connector fitting end 240 is made to have a given configuration that is different from the configuration of a convention luer end, so that it may be connected to or matable with only a counterpart connector fitting having a special configuration that is a mirror counterpart of luer connector fitting end 240. Such connector fitting end having the special configuration is incorporated into the syringe illustrated in FIGS. 15*a* and 15*b*, to be discussed in greater detail, infra.

With reference to FIGS. 11-14, the special configuration fitting end 240 has a base 240*a*, a mid-section 240*b* and a fitting end 240*c*, the same as in the earlier embodiment. Same as the earlier embodiment, the special configuration fitting end 240 may be considered to be an elongate cylindrical extension having a through bore with an opening 242 that leads into the bore of the cylindrical extension. However, rising from the outer wall surface of fitting end 240*c* and away from the distal end 244 of the special configuration fitting end 240 are two protrusions 250*a* and 250*b* in the form of elongate ribs. The protrusions, or elongate ribs 250*a* or 250*b*, each are positioned at fitting end 240*c* in an offset manner from a longitudinal axis 246 along which the special configuration fitting end 240, the catheter end 26 and the flexible tubing 30 that connects both of those fittings are in alignment with. The predetermined distance separating the front edge of the elongate protrusion 250*a* to the distal end 244 of the special configuration fitting end 240 is designated 248, per shown in FIG. 11. Protrusion 250*b* is not shown in FIG. 11 since it is at the opposite side of special configuration fitting end 240.

Figure 15A:
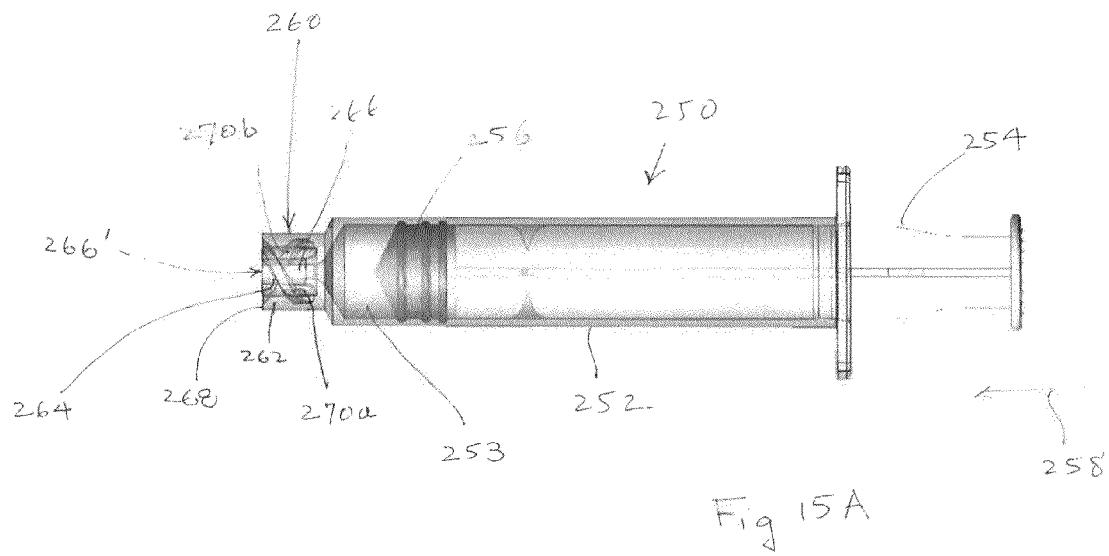
FIGS. 15A and 15B show a syringe with a specially configured connector fitting that allow it and the fitting end of the FIG. 11 adapter device to be connected to each other.
Figure 15B:
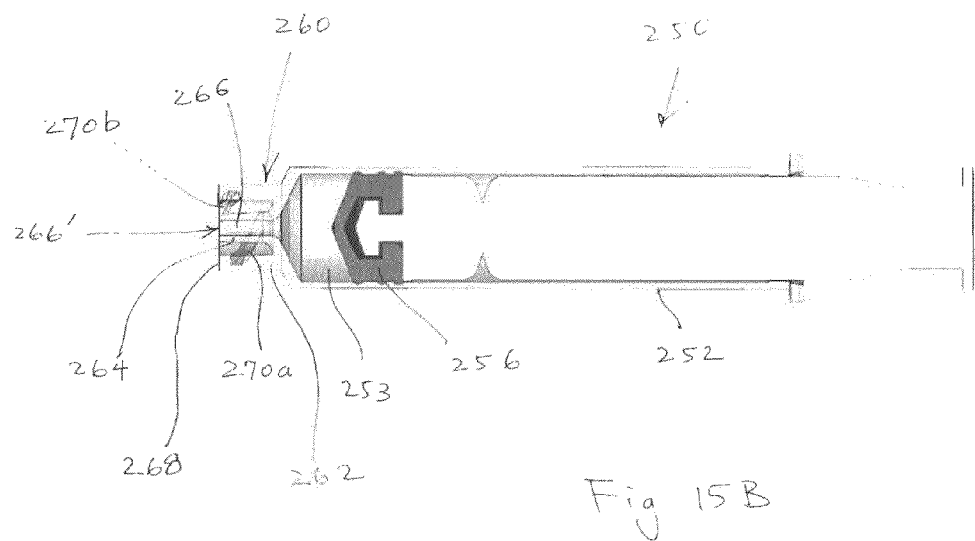

As the elongate protrusions 250*a* and 250*b* are offset from the longitudinal axis 246, those protrusions can readily be threadingly mated to corresponding internal threads of a counterpart connector fitting of a fluid supply or input means discussed above, including for example a fluid store bag, a fluid input line from a pump (not shown) and other equivalent fluid supply or input devices including syringes such as syringe 250 shown in FIGS. 15*a* and 15*b*.

With reference to FIGS. 15*a* and 15*b*, syringe 250 is shown to have a main hollow cylindrical body 252 into which a plunger rod 254 is insertable and slidable therealong. As is well known, plunger rod 254 has an elastomeric, or rubber plunger head 256, that fittingly slides along the internal chamber 253 of syringe body 252. A medicament fluid stored in chamber 253 of syringe 250 may be ejected from the syringe if the plunger 254 were to be pushed relative to body 252 along the direction indicated by directional arrow 258.

Syringe 250 shown in FIGS. 15*a* and 15*b* is a specially designed syringe in that its connector fitting 260 has a special configuration with dimensions that allow it to connect to or mate with only a counterpart specially configured connector fitting, for example the special configuration fitting end 240, more specifically the fitting end 240c having the given configuration, of adapter device 2 shown in FIGS. 11-14. In other words, connector fitting 240 (with fitting end 240c) of adapter 2 and connector fitting 260 of syringe 250 are mirror counterparts of each other. As configured, connector fitting 260 has a circumferential wall 262 that spatially circumscribes a nose extension 264 that has a through passage 266 that extends into chamber 253 of syringe body 252, so that a fluid path is established between mouth 266' of through passage 266 at the distal end 268 of connector fitting 260.

Formed in the inner surface of circumferential wall 262 of connector fitting 260 are two internal threads 270a and 270b each with an opening at distal end 268 of connector fitting 260 to enable protrusions 250a and 250b of special configuration fitting end 240 of adapter 2 to fittingly mate with the connector fitting 260. When turned in one direction, for example the clockwise direction with reference to adapter 2, syringe 250 and adapter 2, more precisely fitting end 240 and connector fitting 260 of adapter 2 and syringe 250, respectively, are lockingly coupled to each other. A rotational movement of syringe 250 in the opposite direction, for example the counterclockwise direction relative to adapter 2, removes syringe 250 from adapter 2. As discussed above, the positioning of protrusions 250a and 250b at the outer surface of fitting end 240c, and the special configuration of the extensional wall 262 of syringe 250 enable those devices to readily mate with each other. Since connector fitting 260 of syringe 250 and end fitting 240 of adapter 2 are formed as corresponding counterpart fittings with non-conventional configurations that can only mate with each other, syringe 250 and adapter 2 each are prevented from mating with devices that have conventional connector fittings, for example the conventional female luer end fitting 24 of the adapter device and the conventional luer male connector 46a of syringe 46 shown in FIG. 3.

Figures 13A, 13B:
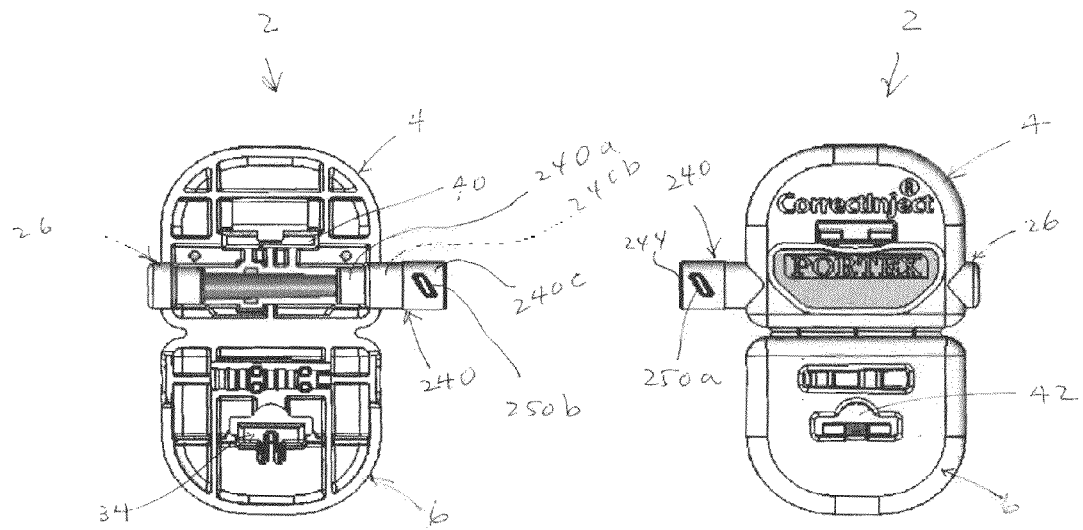
FIGS. 13A and 13B show the inside surface plan view and the outside surface plan view, respectively, of the FIG. 11 device.
Figure 14:
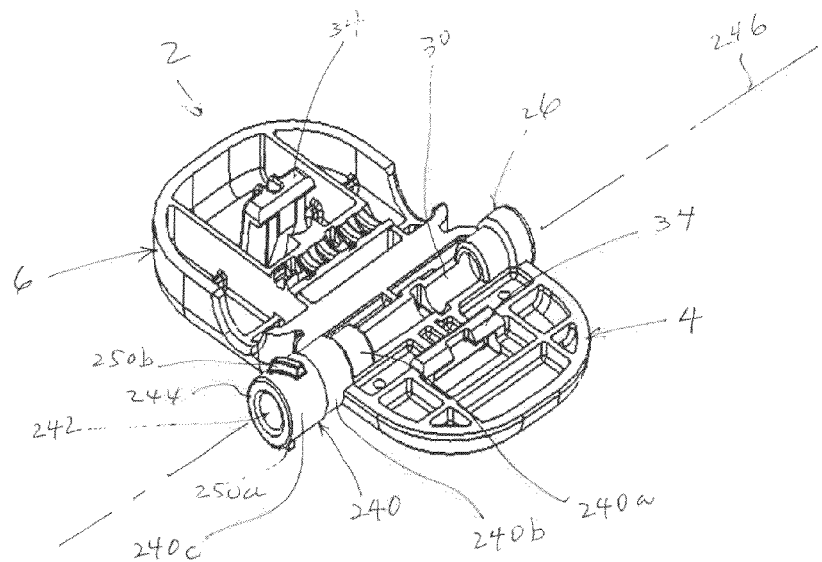
FIG. 14 show a perspective view of the FIG. 11 device with both its shell members in the open position.

In addition to protrusions 250a and 250b being positioned in a particular offset manner at the outer surface of fitting end 240c, opening 242 of special configuration fitting end 240 of adapter 2 has a predetermined or given cross section that prevents it from mating with the nose cone extension of a conventional slip fit type syringe. The cross section of opening 242 may be smaller than the cross section at the tip of the nose cone extension of a conventional luer connector fitting of a fluid store or supply device, for example a slip fit type syringe, so that the conventional nose cone extension cannot enter opening 242. Conversely, opening 242 and the conical inner wall of the through bore of end fitting 240 of adapter 2 may be configured to have a dimension greater than the largest cross section, most likely at the base, of a conventional nose cone extension, so that a conventional nose cone extension cannot fittingly mate with end fitting 240 of adapter 2 due to the conventional nose cone extension of the conventional fluid supply device would readily fall out of opening 242. Putting it differently, the given configuration of special configuration fitting end 240 of the adapter device 2 of FIGS. 13-14 is such that it prevents fitting end 240c from lockingly connect to a counterpart connector fitting that has a conventional locking luer connector or a conventional slip fit luer connector. The cross section of the through bore of connector fitting 240 may increase conically from its opening 244 to its base 240a.

With reference to FIGS. 15a and 15b, the connector fitting 260 of syringe 250 is shown to have both a circumferential wall 262 and a nose cone extension 264 spatially surrounded by wall 262. As discussed above, connector fitting 260 has a special configuration that mirrors the given configuration of the connector end fitting 240 of adapter 2. This means that the configuration of the internal threads 270a and 270b each are such that protrusions 250a and 250b can threadingly mate therewith. Also, the outer circumferential dimension of nose cone 264 is such that when protrusions 250a and 250b are threadingly mated to internal threads 270a and 270b, nose cone extension 264 is fittingly inserted into opening 242 with a tolerance that prevents leakage of fluid between connector fitting 260 and special configuration fitting end 240.

As discussed above, the given configuration of connector end fitting 240 is such that it can accept both a locking type connector fitting or a slip fit type connector fitting. In that regard, assume syringe 250 shown in FIGS. 15a and 15b is without outer wall 262, so that syringe 250 is a slip fit type syringe having only a conical nose extension connector. Given that the nose cone extension 264 is designed to have a special configuration that is a mirror counterpart to the cross sectional dimension of the through passage from opening 242 through special configuration end fitting 240, the non-locking slip fit syringe nonetheless can be mated to adapter 2 having the given configuration at its connector fitting end, as nose cone extension 264 of the syringe (or other fluid supply devices discussed above) is able to enter opening 242 and be frictionally held to end fitting 240 due to the friction between the inner circumferential wall of the through bore of connector end fitting 240 and the outer surface of nose cone extension 264. For a slip type fit, syringe 250 is removable from adapter 2 by simply forcibly pulling nose cone extension 264 away from connector fitting end 240. Also, the protrusions 250a and 250b for the special configuration connector end fitting may be eliminated for the adapter of the instant invention that is to mate with a slip fit type syringe, for those protrusions are superfluous since the coupling of the special connector end fitting of the instant invention with its counterpart special slip fit type syringe is due only to the frictional mating of the nose cone extension of the syringe with the through bore of the connector end fitting.

Inasmuch as the present invention is subject to many variations, modifications and changes in detail, it is intended that the matter described throughout this specification and shown in the accompanying drawings be interpreted as illustrative only and not in a limiting sense. Accordingly, it is intended that the invention be limited only by the spirit and scope of the hereto appended claims.

The invention claimed is:

1. A device for establishing a fluid path, comprising: one and other members each having an inner surface and an outer surface, the one and other members integrally connected at a common hinge and having respective matching peripheries that matchingly abut to form a closed clam shell shaped device that includes a fitting end and an aperture end connected by a tubing so that a through passage is established between the fitting end and the aperture end, the aperture end adapted to accept a fluid output line, the one and other members having respective first and second latch mechanisms that cooperate to lockingly couple the one and other members to each other when the one and other members are folded along the common hinge towards each other, the folded one and other members enclosing the tubing and fixedly holding the fluid output line to the aperture end, the fitting end having a given configuration that varies from a conventional luer end such that the fitting end is matable only with a connector fitting having a special configuration that is a counterpart to the given configuration.

2. The device of claim 1, wherein the given configuration of the fitting end comprises a through bore cylindrical extension having an outer wall and a distal end with an opening, at least one protrusion formed on the outer wall of the cylindrical extension a predetermined distance away from the distal end of the cylindrical extension.

3. The device of claim 2, wherein the fitting end has a longitudinal axis where along the cylindrical extension extends, and wherein the at least one protrusion comprises an elongate rib rising from the outer wall of the cylindrical extension positioned offset from the longitudinal axis of the cylindrical extension.

4. The device of claim 2, wherein the fitting end is matable with a fluid supply means that has the connector fitting having a circumferential wall with an internal thread that is threadedly matable with the at least one protrusion in a locking relationship to thereby connect the fluid supply means to the device, the connector fitting not matable with a conventional counterpart fitting.

5. The device of claim 1, wherein the given configuration of the fitting end comprises a through bore cylindrical extension having an outer wall and a distal end with an opening, two protrusions formed on opposite sides of the outer wall of the cylindrical extension a predetermined distance away from the distal end of the cylindrical extension.

6. The device of claim 5, wherein the fitting end has a longitudinal axis where along the cylindrical extension extends, and wherein the two protrusions comprise two elongate ribs rising from opposite sides of the outer wall of the cylindrical extension, each of the ribs positioned offset from the longitudinal axis of the cylindrical extension.

7. The device of claim 1, wherein the given configuration of the fitting end comprises a through bore cylindrical extension having a distal end with an opening, the opening configured to have a cross sectional dimension that prevents the opening from mating with a conventional fitting but enables the opening to mate with the counterpart connector fitting having a particular conical configuration.

8. The device of claim 7, wherein the fitting end is matable with a fluid supply means having the connector fitting with a nose extension of the particular conical configuration so that the nose extension is readily slip fitted into the opening of the cylindrical extension to mate with the fitting end, the nose extension of the particular conical configuration not matable with a conventional counterpart fitting.

9. An apparatus for coupling a catheter to a fluid supply device having a connector fitting with a special configuration, comprising: a one piece clam shell shaped adapter having one shell and other shell integrally attached to and foldable towards each other about a living hinge to a closed position, the one shell and the other shell having respective matching peripheries that matchingly abut to form a closed container when the one and other shells are in the closed position, the one shell and the other shell each have an inner surface and an outer surface, the one shell having formed thereat a fitting end and an aperture end connected by a tubing at the inner surface thereof so that a through passage is established between the fitting end and the aperture end, the aperture end adapted to accept the catheter input to the tubing, the fitting end having a given configuration that is a counterpart of the special configuration to enable the fitting end to mate with the connector fitting of the fluid supply device, the given configuration of the fitting end preventing the fitting end from mating with a conventional counterpart fitting, a first latch mechanism at the one shell lockingly engaging a second latch mechanism at the other shell when the one and other shells are folded along the living hinge to close upon each other, a retainer structure at the inner surface of the other shell to fixedly hold the catheter when the first and second latch mechanisms are engaged to each other.

10. The apparatus of claim 9, wherein the given configuration of the fitting end comprises a through bore cylindrical extension having an outer wall and a distal end with an opening, two protrusions formed on opposite sides of the outer wall of the cylindrical extension a predetermined distance away from the distal end of the cylindrical extension.

11. The apparatus of claim 10, wherein the fitting end has a longitudinal axis where along the cylindrical extension extends, and wherein the two protrusions comprise two elongate ribs rising from opposite sides of the outer wall of the cylindrical extension, each of the ribs positioned offset from the longitudinal axis of the cylindrical extension.

12. The apparatus of claim 10, wherein the fitting end is matable with the fluid supply device, the connector fitting of the fluid supply device having a circumferential wall with an internal thread that is threadedly matable with the protrusions in a locking relationship, the connector fitting not matable with another conventional counterpart fitting.

13. The apparatus of claim 9, wherein the given configuration of the fitting end comprises a through bore cylindrical extension having a distal end with an opening, the opening having a cross sectional dimension configured to prevent ft the opening from mating with the conventional counterpart fitting but enables the opening to mate with a counterpart connector fitting having a particular conical configuration.

14. The apparatus of claim 13, wherein the fitting end is matable with a nose extension of the connector fitting of the fluid supply device, the nose extension having the particular conical configuration so that the nose extension is readily slip fitted into the opening of the cylindrical extension, the nose extension of the particular conical configuration not matable with another conventional counterpart fitting.

15. A system, comprising:
a fluid output device;
a fluid input means having a connector fitting with a special configuration that prevents the connector fitting from mating with a conventional counterpart fitting;
a clam shell shaped adapter having one shell and other shell integrally attached to and foldable towards each other about a living hinge and having respective matching peripheries that matchingly abut to form a closed container when the one shell and the other shell are folded onto each other, the one shell and the other shell each have an inner surface and an outer surface, the one shell having formed thereat a fitting end and an aperture end connected by a tubing to establish a through passage between the fitting end and the aperture end, a first latch mechanism at the one shell lockingly engaging a second latch mechanism at the other shell when the one and other shells are folded along the living hinge to close upon each other;
wherein the fluid output device is matable to the aperture end; and
wherein the fitting end has a given configuration that is a counterpart to the special configuration of the connector fitting at the fluid input means so that the fitting end is matable with the connector fitting of the fluid input means, the given configuration of the fitting end preventing the fitting end from mating with another conventional counterpart fitting;
whereby a fluid path between the fluid input means and the fluid output device is established by the adapter when the fluid output device is mated with the aperture end and the connector fitting of the fluid input means is mated with the fitting end.

16. The system of claim 15, wherein the given configuration of the fitting end comprises a through bore cylindrical extension having an outer wall and a distal end with an opening having a given cross section, and respective protrusions formed on opposite sides of the outer wall of the cylindrical extension a predetermined distance away from the distal end of the cylindrical extension.

17. The system of claim 16, wherein the fitting end has a longitudinal axis where along the cylindrical extension extends, and wherein the respective protrusions each comprise an elongate rib rising from a side of the outer wall of the cylindrical extension positioned offset from the longitudinal axis of the cylindrical extension.

18. The system of claim 16, wherein the fluid input means comprises a syringe, a fluid bag or a fluid line; and
  wherein the fitting end is matable with the syringe, the fluid bag or the fluid line each having the connector fitting having a circumferential wall with an internal thread threadedly matable with the protrusions in a locking relationship, the connector fitting not matable with the conventional counterpart fitting.

19. The system of claim 15, wherein the given configuration of the fitting end comprises a through bore cylindrical extension having a distal end with a given opening, the opening having a cross section configured to prevent the opening from mating with the another conventional counterpart fitting;
  wherein the connector fitting of the special configuration of the fluid input means comprises a conical nose having a special dimension that enables the conical nose and the given opening of the fitting end to mate to each other; and
  wherein the fitting end of the adapter is incompatible with the another conventional counterpart fitting and the connector fitting of the fluid input means is incompatible with the conventional counterpart fitting.

20. The system of claim 15, wherein the fluid input means comprises a syringe, a fluid bag or a fluid line and wherein the given configuration of the fitting end comprises a through bore cylindrical extension having a distal end with an opening having a given cross section, and
  wherein the fitting end is matable with the syringe, the fluid bag or the fluid line each having a conical nose extension having the special configuration, the conical nose extension of the syringe, the fluid bag or the fluid line is readily slip fitted into the opening of the cylindrical extension, the conical nose extension of the syringe, the fluid bag or the fluid line not matable with the conventional counterpart fitting.

* * * * *